United States Patent [19]

Okada et al.

[11] 4,349,625

[45] Sep. 14, 1982

[54] METHOD FOR ASSAYING FATTY ACIDS

[75] Inventors: Tsutomu Okada, Yokohama; Tadashi Hishida, Tokyo; Minoru Muramatsu, Yokohama, all of Japan

[73] Assignee: Mitsubishi Chemical Industries Limited, Tokyo, Japan

[21] Appl. No.: 145,035

[22] Filed: Apr. 30, 1980

[30] Foreign Application Priority Data

May 25, 1979 [JP] Japan .................................. 54-64651
Sep. 25, 1979 [JP] Japan ................................ 54-122961

[51] Int. Cl.$^3$ ......................... C12Q 1/28; C12Q 1/00; C12Q 1/48; C12Q 1/32
[52] U.S. Cl. ......................................... 435/4; 435/15; 435/25; 435/26; 435/28; 435/805
[58] Field of Search .................. 435/4, 15, 25, 26, 28, 435/805, 810; 23/230 B, 230 R; 424/27

[56] References Cited

U.S. PATENT DOCUMENTS 4,071,413 1/1978 Takahashi et al. ...................... 435/4
4,301,244 11/1981 Kikuchi et al. ......................... 435/4

FOREIGN PATENT DOCUMENTS 1219885 1/1971 United Kingdom .

OTHER PUBLICATIONS

Zwierzykowski, et al., "Fractionation of fatty acids involving the use of surfactants and the selection of these for rape seed oil fatty acids as an example", *Chem. Absts.* vol. 81, No. 24, (1974), p. 150, Abs. #15496Fe.

Shimizu et al., "Enzymatic Microdetermination of Serum Free Fatty Acids", *Anal. Biochem*, vol. 98, No. 2, (1979), pp. 341–345.

Lagercrantz, et al., "Binding of Some Fatty Acids and Drugs to Immobilized Bovine Serum Albumin Studied by Affinity Chromatography" *Anal. Biochem*, vol. 99, (1979), pp. 352–364.

Meinertz, "Analytical Procedures for Free Fatty Acids", *Progr. Biochem Pharmacol*, vol. 6, (1971), pp. 317–367.

*Primary Examiner*—Thomas G. Wiseman
*Attorney, Agent, or Firm*—Oblon, Fisher, Spivak, McClelland & Maier

[57]            ABSTRACT

There is disclosed a method for assaying fatty acids in a system containing albumin together with the fatty acids using acyl-CoA synthetase, characterized by performing the assay in the presence of a water-soluble salt of a dibasic fatty acid having 10 to 18 carbon atoms or a benzenesulfonate optionally having one or more $C_1$–$C_5$ side chains.

9 Claims, No Drawings

METHOD FOR ASSAYING FATTY ACIDS

BACKGROUND OF THE INVENTION

1. Field of the Invention

This invention relates to a method for the quantitative determination of free fatty acids (abbreviated throughout the specification and claims as FFA) using an enzyme. The term "free fatty acids" or "FFA" used herein is intended to include any fatty acid whose carboxyl group is not covalently bonded to another compound.

2. Description of the Prior Art

Conventional methods for assaying FFA include the Dore's method wherein FFA is extracted into an organic solvent and titrated with a dilute alkali, the Itaya's method wherein metal salts of FFA are extracted into an appropriate solvent and assayed colorimetrically, and the like. These methods, however, were difficult to standardize because of complicated procedures involved in the extraction with an organic solvent and other problems.

A method for the assay of FFA using an enzyme is reported by Takahashi et al. in Rinsho Kagaku Vol. 4, No. 2, pages 179-185 (1975), which method employs acyl-CoA synthetase enzyme (E.C. 6.2.1.3; hereinafter abbreviated as ACS). Use of enzymes in assay systems has various advantages including the fact that the reactions involved are specific and proceed under mild conditions, and in recent years such enzymatic methods have found particularly wide applications. However, these prior art assay methods using enzymes were difficult to apply to assay for FFA in a system which contains in addition to FFA a protein, particularly such a protein as albumin having a strong affinity for FFA, for example, to assay for serum FFA, since FFA is firmly bound to albumin in such a system and is not readily set free under mild conditions as employed in practice of enzymatic reactions. The nature of the linkage between FFA and albumin is not exactly understood, although it is said to be a hydrophobic bond or an ionic bond.

SUMMARY OF THE INVENTION

Upon extensive investigation, it has been found that water-soluble salts of $C_{10}$–$C_{18}$ dibasic fatty acids and salts of benzenesulfonic acids optionally having one or more $C_1$–$C_5$ side chains are effective for cleavage or dissociation of the linkage of FFA to a protein having a strong affinity for FFA, particularly the linkage of FFA to albumin, with an increased rate of reaction. Thus, in accordance with the invention, there is provided a method for enzymatically assaying fatty acids in a system containing albumin together with the fatty acids, characterized by performing the assay in the presence of a water-soluble salt of a dibasic fatty acid having 10 to 18 carbon atoms or a benzenesulfonate optionally having one or more $C_1$–$C_5$ side chains.

DETAILED DESCRIPTION OF THE PREFERRED EMBODIMENTS

In the method for the enzymatic assay for fatty acids according to the invention, ACS is preferably used as the enzyme.

The assaying procedure is not critical and any procedure using ACS may be employed. For example, the amount of adenosine monophosphate (hereinafter abbreviated as AMP) formed from FFA by an ACS-catalyzed reaction represented by the following Equation (1) is converted into the amount of NADH decreased correspondingly, which is determined from difference in UV absorbance and from which the amount of FFA is calculated (Procedure A). Alternatively, acyl-CoA formed from FFA by the same ACS-catalyzed reaction is converted with acyl-CoA oxidase into $H_2O_2$, the latter is in turn converted into a quinone dye having an absorption band in the visible region and the amount of FFA is calculated from the absorbance measured in the visible region (Procedure B).

(1) 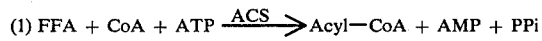

Procedure A (2) 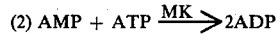

(3) 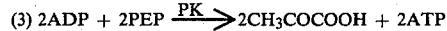

(4) 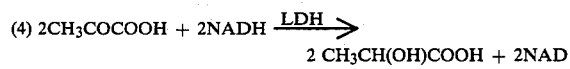

Procedure B (5) 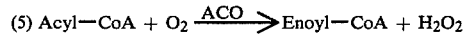

(6) 

In these equations, the following abbreviations are used:
CoA = Coenzyme A
ATP = Adenosine triphosphate
PPi = Pyrophosphoric acid
MK = Myokinase (E.C. 2.7.4.3)
ADP = Adenosine diphosphate
PEP = Phosphoenolpyruvate
PK = Pyruvate kinase (E.C. 2.7.1.40)
NADH = Reduced nicotinamide-adenine dinucleotide
NAD = Nicotinamide-adenine dinucleotide (oxidized)
LDH = Lactate dehydrogenase (E.C. 1.1.1.27)
ACO = Acyl-CoA oxidase
4-AA = 4-Aminoantipyrine
AADA = 3-Acetamino-N,N-diethylaniline
POD = Peroxidase The species of ACS used in the assay method according to the invention is not critical, but preferably it is selected in such a way that the dissociating agent used in the assay is by no means the substrate thereof and that its activity is not readily inhibited by the dissociating agent. These ACS species can be selected from those of animal and microorganism origin. In practice, ACS species of microorganism origin are preferred because of their suitability for mass production.

The compound used as a dissociating agent in practice of the invention is a water-soluble salt of a dibasic fatty acid having 10 to 18 carbon atoms or a benzenesulfonate optionally having one or more $C_1$–$C_5$ side chains. Specific examples of the former compound are alkali metal salts such as sodium and potassium salts and ammonium salts of sebacic acid, 1,9-nonamethylenedicarboxylic acid, 1,10-decamethylenedicarboxylic acid, 1,11-undecamethylenedicarboxylic acid (brassylic acid), 1,12-dodecamethylenedicarboxylic acid, 1,13-tridecamethylenedicarboxylic acid, 1,14-tetradecamethylenedicarboxylic acid, 1,15-pentadecamethylenedicarboxylic acid, 1,16-hexademethylenedicarboxylic acid and the like. Salts of dibasic fatty acids having not more than 9 carbon atoms exert only weak dissociation action on the FFA-albumin linkage, whereas a dissociating agent comprising a salt of a dibasic fatty acid having 19 or more carbon atoms has a low solubility in water and may possibly be precipitated during the reaction to produce a turbidity which interfere with optical measurement.

The amount of a water-soluble salt of a dibasic fatty acid added to the assay system varies depending on its intended effect, solubility, influence on the enzyme used in the assay and other factors. In general, this amount is preferably about 5 to 1000 times the amount of FFA on the molar basis and when expressed as a concentration in the enzymatic reaction system, it is preferably of the order of $1 \times 10^{-4}$ to $1 \times 10^{-1}$ mol/l.

Specific examples of the benzenesulfonate optionally having one or more $C_1$-$C_5$ side chains are sodium, potassium and ammonium salts of benzenesulfonic acid, p-toluenesulfonic acid, p-ethylbenzenesulfonic acid, p-n-propylbenzenesulfonic acid, p-n-amylbenzenesulfonic acid, 2,4-dimethylbenzenesulfonic acid, 2,5-dimethylbenzenesulfonic acid and the like. A benzenesulfonate having a side chain of six or more carbon atoms does exert a dissociation action on the FFA-albumin linkage, but at the same time it exerts an increased inhibitory effect on the enzyme activity and in this respect involves a problem in practical application.

The amount of a benzenesulfonate added to the assay system also varies depending on its intended effect, solubility, influence on the enzyme used and other factors.

In general, the benzenesulfonate is preferably added at a molar ratio of benzenesulfonate to FFA to be assayed of about 5:1 to 1000:1, or expressed in another way it is preferred that the benzenesulfonate be present at a concentration of about 0.01 to 5% in the assay system. The dissociating agent used in the invention may be introduced into the assay system by adding it to any of a FFA-containing sample and various reagents used in the assay including the enzyme. Alternatively, if desired, it may be added directly to the system just before the measurement.

It is described in Japanese Patent Publication No. 35715/1974 entitled "Method for the Detection of Hydrogen Peroxide" that an anionic surfactant is added to a detection system of hydrogen peroxide which resorts to color development with an indicator system. However, the concept disclosed in the above patent has no relevance to the present invention. An essential feature of the invention resides in dissociation or cleavage of the FFA-albumin linkage formed in an assay system for FFA in which ACS is employed. Therefore, the invention is in itself irrespective of procedure employed for detection of FFA, whether the procedure is the aforesaid Procedure A wherein decrease in UV absorbance of NADH is measured or Procedure B wherein a dye is formed with $H_2O_2$. Also it is noted that the compounds used as dissociating agents according to the invention exert so weak anionic surface activities that they are usually not regarded as anionic surfactants. For example, it is described in Kaimen-Kasseizai Binran (Handbook of Surfactants), edited by I. Nishi et al., Sangyo-Tosho, Tokyo, page 129 (1960) that sodium n-butyl- and n-amylbenzenesulfonate have no ability in micelle formation.

Thus, in accordance with the method of the invention, FFA can be assayed precisely by simple procedures without interference from albumin.

Having generally discribed this invention, a more complete understanding can be obtained by reference to certain preparations and reference examples which are provided herein for purpose of illustration only and are not intended to be limiting in any manner.

Preparation 1 (Preparation of ACS)

Following the procedures described in European Journal of Biochemistry, 93, 197–203 (1979), ACS from Candida lipolytica NRRL Y-6795 was purified by subjecting it successively to treatment with Triton X-100 (non-ionic surfactant available from Rohm & Haas), chromatography on a phosphocellulose column and chromatography on a Blue-Sepharose (a trademark, Pharmacia Fine Chemicals) column. The purified ACS was used as a solution in 50% glycerine containing 10 mM potassium phosphate buffer pH 7.4, 0.063% Triton X-100 and 2.5 mM 2-mercaptoethanol.

Preparation 2 (Preparation of ACO)

Using a partial modification of the procedure described in the collected synopses of lectures in the 1979 annual meeting in Toyama of the Lipid Biochemical Society in Japan, page 144, acyl-CoA oxidase (ACO) from Candida utilis IFO 0396 was purified by fractionation with ammonium sulfate and chromatography on a DEAE-Sephadex column and used as a suspension in 50% saturated ammonium sulfate containing 50 mM potassium phosphate buffer pH 7.4.

EXAMPLE 1

The reagents used in this example were as follows:

(a) Buffer 100 mM Tris-HCl buffer pH 8.0 containing 2 mg/ml of Triton X-100, 2 mM 2Na-EDTA (disodium ethylenediaminetetraacetate) and 10 mM $MgCl_2$.

(b) Enzyme-substrate solution 40 mg of ATP disodium salt, 50 mg of potassium phosphoenolpyruvate, 20 U of myokinase (available from Boehringer Mannheim (B.M.), grade I), 15 U of pyruvate kinase (available from B.M., grade II) and 15 U of lactate dehydrogenase (available from B.M., derived from rabbit muscle) are dissolved in 1 ml of the above-mentioned buffer.

(c) NADH solution

In 1 ml of the above buffer, 3 mg of NADH disodium salt is dissolved.

(d) CoA (Coenzyme A) solution

In 1 ml of the above buffer, 12.5 mg of CoA lithium salt is dissolved.

(e) ACS solution

An ACS solution in 50% glycerine in a concentration of about 4 U/ml as prepared in Preparation 1 which is diluted with three volumes of water is used.

(f) FFA solution

Aqueous 0.5 mM potassium oleate solution is used. In a microcell of 10 mm in thickness (light pass length) and 5 mm in width, 50 μl of a sample containing 0.5 mM FFA and 2.5% (W/V) human serum albumin was placed and 1.0 ml of the buffer solution and 50 μl each of a solution of dissociating agent at a predetermined concentration, the NADH solution, the enzyme-substrate solution and the ACS solution were added. The content of the microcell was then preheated at 37° C. in a spectrophotometer (Shimadzu, model UV-200) equipped with a thermostated cell holder. Thereafter 20 μl of the CoA solution was added to initiate the reaction and decrease in optical density (OD) at 340 nm was recorded with the elapse of time. From the data, the value of maximum ΔOD/min was calculated. The results are given in Table 1 below.

As is apparent from Table 1, addition of a salt of a $C_{10}$–$C_{18}$ dibasic fatty acid or of a benzenesulfonate provided a higher rate of decrease in ΔOD or a higher rate of reaction than the control in which only albumin was added, and this indicates that such addition made FFA more reactive.

TABLE 1

| No.** | Dissociating agent | Concentration mM | ΔOD$_{340}$/min |
|---|---|---|---|
| 1 | None (albumin not added) | 0 | 0.076 |
| 2 | None (albumin added)* | 0 | 0.019 |
| 3 | Potassium salt of tetramethylenedicarboxylic acid | 25 | 0.015 |
| 4 | Potassium salt of hexamethylenedicarboxylic acid | 25 | 0.015 |
| 5 | Potassium salt of 1,8-octamethylenedicarboxylic acid | 25 | 0.026 |
| 6 | Potassium salt of decamethylenedicarboxylic acid | 5 | 0.028 |
| 7 | Potassium salt of decamethylenedicarboxylic acid | 10 | 0.031 |
| 8 | Potassium salt of decamethylenedicarboxylic acid | 20 | 0.034 |
| 9 | Potassium salt of 1,11-undecamethylenedicarboxylic acid | 5 | 0.035 |
| 10 | Potassium salt of 1,11-undecamethylenedicarboxylic acid | 10 | 0.040 |
| 11 | Potassium salt of 1,11-undecamethylenedicarboxylic acid | 20 | 0.045 |
| 12 | Dipotassium 1,12-dodecamethylenedicarboxylate | 2.5 | 0.041 |
| 13 | Dipotassium 1,12-dodecamethylenedicarboxylate | 10 | 0.048 |
| 14 | Dipotassium 1,14-tetradecamethylenedicarboxylate | 2.5 | 0.045 |
| 15 | Dipotassium 1,16-hexadecamethylenedicarboxylate | 2.5 | 0.032 |
| 16 | Sodium p-toluenesulfonate | 100 | 0.030 |
| 17 | Sodium p-n-amylbenzenesulfonate | 50 | 0.030 |

*In all runs from No. 2 to No. 17 albumin was added.
**Runs from No. 1 to No. 4 are beyond the scope of the invention and the remaining runs (No. 5 through No. 17) fall within the scope of the invention.

EXAMPLE 2

The runs of Example 1 were repeated with the same compositions of the reaction system as in Example 1 except that the samples containing FFA or FFA plus albumin were replaced by human serum samples.

The reaction was continued for 15 minutes at 37° C., and the OD$_{340}$ values were read just before the addition of CoA solution and 15 minutes later when the reaction was almost complete and decrease in OD ceased. As a sample blank distilled water was substituted for the ACS solution in the reaction systems and the reaction and measurement of OD were carried out in the same way.

The concentration of FFA in a serum sample was calculated by the following equation:

FFA in serum (μmol/ml)

$$= \{(C - D) - (B - A)\} \times \frac{\text{Total volume (ml)}}{\text{volume of sampled serum (ml)}}$$

$$\times \frac{1}{\text{Theoretical decrease in OD}_{340} \text{ of NADH attributable to 1 μmol/ml of FFA}}$$

$$= \{(C - D) - (B - A)\} \times \frac{1.22}{0.05} \times \frac{1}{2 \times 6.22}$$

$$= \{(C - D) - (B - A)\} \times 1.96$$

where:
A = OD$_{340}$ of the reaction system just before the addition of CoA solution;
B = OD$_{340}$ of the reaction system after 15 minutes
C = OD$_{340}$ just before the addition of CoA solution in the blank run, and
D = OD$_{340}$ after 15 minutes in the blank run.
The results are given in Table 2 below.

When the solution of dissociating agent which caused cleavage of the FFA-albumin linkage was replaced by the same volume (50 μl) of demineralized water, the reaction did not go to completion even after 20 minutes and no serum sample could be assayed for FFA.

TABLE 2

| Serum | Dissociating agent | Conc. of solution of Dissociating agent, mM | FFA assayed μmol/ml | FFA assayed by extraction method μmol/ml |
|---|---|---|---|---|
| A | Dipotassium 1,11-undecamethylenedicarboxylate | 20 | 1500 | 1475 |
| B | " | 20 | 340 | 370 |
| B | Dipotassium 1,10-decamethylenedicarboxylate | 50 | 335 | 370 |
| B | Dipotassium 1,14-tetradecamethylenedicarboxylate | 10 | 340 | 370 |
| C | Dipotassium 1,11-undecamethylenedicarboxylate | 20 | 570 | 560 |
| C | Dipotassium 1,12-dodecamethylenedicarboxylate | 20 | 575 | 560 |
| C | Dipotassium 1,14-tetradecamethylenedicarboxylate | 10 | 570 | 560 |
| C | Sodium p-toluenesulfonate | 1000 | 585 | 560 |

EXAMPLE 3

The reagents used were as follows:

(a) Buffer (1)

100 mM Tris-HCl buffer pH 8.0 containing 3.2 mM Triton X-100, 2 mM disodium ethylenediaminetetraacetate and a dissociating agent such as a benzenesulfonate.

(b) Buffer (2)

100 mM Tris-HCl buffer pH 8.0 containing 60 mM magnesium chloride.

(c) Enzyme solution (1)

A solution of 80 mg of ATP disodium salt and 20 U of myokinase dissolved in 40 ml of Buffer (1).

(d) Enzyme solution (2)

Prepared by adding 5 ml of the ACS solution in 50% glycerine with a concentration of about 4 U/ml as prepared in Preparation 1 to a solution of 25 mg of CoA in 5 ml of Buffer (2).

(e) Enzyme solution (3)

A suspension of ACO in 50% saturated ammonium sulfate having a concentration of about 50 U/ml and prepared as described in Preparation 2.

(f) Color developing solution 100 mM phosphate buffer pH 7.4 containing 0.05 mg/ml of 4-aminoantipyrine, 0.05% 3-acetamino-N,N-diethylaniline, 5 U/ml of a peroxidase (available from Sigma, Type II) and 0.5 mM N-ethylmaleimide, prepared by a modification of the method described in Analytical Clinical Biochem. 6, 24 (1969).

A mixture of 100 μl of a sample containing 280 μM potassium oleate and 2.5% human serum albumin, 400 μl of Enzyme Solution (1) and 100 μl of Enzyme Solution (2) was kept at 37° C. for 15 minutes. Subsequently 2 ml of the color developing solution and 10 μl of Enzyme Solution (3) were added and the mixture was kept at 37° C. for an additional 5 minutes. The reaction solution was placed into a cell having a thickness of 10 mm and the value (A) for optical density at 535 nm was measured. As a control, the sample was replaced by the same volume of water and the optical density value (B) was measured in the same way.

An aqueous potassium oleate solution which is free from albumin was separately prepared as a standard solution. This solution was substituted for the sample and the optical density value (C) was also measured in the same way.

The concentration of FFA in the sample was calculated by the following equation:

FFA content of sample $$= \frac{A - B}{C - B} \times \text{(FFA content of standard solution)}$$

The results are summarized in Table 3.

TABLE 3

| Dissociating agent and its concentration in assay system | ΔOD$_{535}$ | FFA μmol/ml |
| --- | --- | --- |
| Sodium p-toluenesulfonate, 0.5% | 0.078 | 260 |

TABLE 3-continued

| Dissociating agent and its concentration in assay system | ΔOD$_{535}$ | FFA μmol/ml |
| --- | --- | --- |
| None | −0.016 | — |

In the reagent system used in this example, myokinase was added in order to completely shift the equilibrium of the foregoing Reaction Equation (1) in favor of acyl-CoA formation by converting AMP which is a product of the ACS-catalyzed reaction expressed by Equation (1) into ADP. The N-ethylmaleimide was added as a CoA-binding agent in order to prevent the hydrogen peroxide ($H_2O_2$) formed in Equation (5) from being consumed by the remaining CoA.

EXAMPLE 4

The reagents used were identical to those used in Example 3. A mixture of 50 μl of a standard serum as a sample, 400 μl of Enzyme Solution (1) containing 125 mM sodium p-toluenesulfonate and 100 μl of Enzyme Solution (2) was kept at 37° C. for 15 minutes. Thereafter 2.5 ml of the color developing solution and 10 μl of Enzyme Solution (3) were added and the mixture was kept at 37° C. for an additional 5 minutes. Subsequently, the fatty acid content of the standard serum was determined in the same manner as described in Example 3. The results obtained with various standard serum samples are given in Table 4.

TABLE 4

| | FFA in sample, μmol/ml | |
| --- | --- | --- |
| Sample | Indicated | Assayed |
| Serum A | 420–580 | 493 |
| Serum B | 480–720 | 697 |
| Serum C | 610–850 | 795 |
| Serum D | 680–920 | 890 |

EXAMPLE 5

Following the procedure of Example 4 except that the dissociating agent is either sodium p-toluenesulfonate or dipotassium 1,11-undecamethylenedicarboxylate, a standard serum (Serum C used in Example 4) as a sample was assayed for FFA in order to compare these two dissociating agents. The results are given in Table 5.

TABLE 5

| Dissociating agent | Conc. in assay System, mM | FFA assayed μmol/ml |
| --- | --- | --- |
| Sodium p-toluenesulfonate | 100 | 783 |
| Dipotassium 1,11-undecamethylenedicarboxylate | 10 | 795 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a method for assaying fatty acids in an aqueous system containing albumin free fatty acid in a sample by reacting, the free fatty acid with adenosine triphosphate in the presence of coenzyme A catalyzed by acyl-CoA synthetase thereby forming AMP and acyl-CoA and measuring the acyl-CoA or AMP formed, the improvement comprising: adding from 0.01 to 5 mole percent, based on said fatty acid, of a water soluble salt of a dibasic fatty acid having 10 to 18 carbon atoms or a salt selected from the group consisting of the sodium, potassium and ammonium salts of benzene sulfonic acid, p-toluene-sulfonic acid, p-ethylbenzenesulfonic acid, p-n-propylbenzenesulfonic acid, p-n-amylbenzenesulfonic acid, 2,4-dimethylbenzenesulfonic acid or 2,5-dimethylbenzenesulfonic acid to the aqueous assay medium.

2. The method of claim 1, wherein said measurement is by optical measuring means.

3. The method of claim 2, wherein said optical measuring means utilizes visible light.

4. The method of claim 2 wherein said optical measuring means utilizes ultraviolet light.

5. The method of claim 3, wherein said salt is that of a dibasic fatty acid having 10 to 18 carbon atoms.

6. The method of claim 5, wherein the concentration of said salt in said assay solution ranges from $1 \times 10^{-4}$ to $1 \times 10^{-1}$ mole/l.

7. The method of claim 5, wherein said salt is selected from the group consisting of the sodium, potassium and ammonium salts of sebacic acid, 1,9-nonamethylenedicarboxylic acid, 1,10-decamethylenedicarboxylic acid, 1,11-undecamethylenedicarboxylic acid, 1,12-dodecamethylenedicarboxylic acid, 1,13-tridecamethylenedicarboxylic acid, 1,14-tetradecamethylenedicarboxylic acid, 1,15-pentadecamethylenedicarboxylic acid and 1,16-hexamethylenedicarboxylic acid.

8. In a method for assaying fatty acids in an aqueous system containing albumin by reacting free fatty acid in a sample with adenosine triphosphate in the presence of coenzyme A catalyzed by acyl-CoA synthetase thereby forming adenosine monophosphate and acyl-CoA in the presence of acyl-CoA oxidase as a catalyst thereby producing hydrogen peroxide as a product which in turn oxidizes a mixture of 4-aminoantipyrine and 3-acetamino-N,N-diethylaniline to quinone dye, and determining the amount of free fatty acid in said sample by measuring the amount of quinoid dye produced, the improvement comprising:

adding from 0.01 to 5 mole %, based on said fatty acid, of a water soluble salt of a dibasic fatty acid having 10 to 18 carbon atoms or a salt selected from the group consisting of the sodium, potassium and ammonium salts of benzenesulfonic acid, p-toluenesulfonic acid, p-ethylbenzenesulfonic acid, p-n-propylbenzenesulfonic acid, p-n-amylbenzenesulfonic acid, 2,4-dimethylbenzenesulfonic acid and 2,5-dimethylbenzenesulfonic acid to the aqueous assay medium.

9. In a method for assaying fatty acids in an aqueous system containing albumin by reacting free fatty acid in a sample with adenosine triphosphate in the presence of coenzyme A catalyzed by acyl-CoA synthetase thereby forming adenosine monophosphate and acyl-CoA, forming pyruvic acid from a series of reactions in a quantity dependent upon the amount of said adenosine monophosphate produced and determining the amount of free fatty acid in said sample by measuring the amount of NADH consumed in the reaction with pyruvic acid, the improvement comprising:

adding from 0.01 to 5 mole %, based on said fatty acid, of a water soluble salt of a dibasic fatty acid having 10 to 18 carbon atoms or a salt selected from the group consisting of the sodium, potassium and ammonium salts of benzenesulfonic acid, p-toluenesulfonic acid, p-ethylbenzenesulfonic acid, p-n-propylbenzenesulfonic acid, p-n-amylbenzenesulfonic acid, 2,4-dimethylbenzenesulfonic acid and 2,5-dimethylbenzenesulfonic acid to the aqueous assay medium.

* * * * *